United States Patent
Suekane et al.

(10) Patent No.: US 6,547,772 B1
(45) Date of Patent: Apr. 15, 2003

(54) SANITARY NAPKINS PROVIDED WITH WINGS

(75) Inventors: Makoto Suekane, Kagawa-ken (JP); Tatsuya Tamura, Kagawa-ken (JP); Kazuya Nishitani, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/487,211

(22) Filed: Jan. 19, 2000

(30) Foreign Application Priority Data

Jan. 20, 1999 (JP) .......................................... 11-012534

(51) Int. Cl.[7] .............................................. A61F 13/15
(52) U.S. Cl. ............................. 604/385.04; 604/385.01; 604/385.03; 604/351; 604/387; 604/385.201; 156/63
(58) Field of Search ........................... 604/351, 385.01, 604/385.03, 385.04, 385.11, 385.16, 385.201, 387, 551; 156/63

(56) References Cited

U.S. PATENT DOCUMENTS 5,447,507 A  9/1995  Yamamoto
5,616,201 A * 4/1997  Finch ..................... 156/73.01
5,772,650 A * 6/1998  Mizutani ................... 604/387
5,824,004 A * 10/1998  Osborn ................ 604/385.02

FOREIGN PATENT DOCUMENTS

| EP | 0 650 714 | 5/1995 | |
| EP | 0 681 821 | 11/1995 | |
| EP | 0800807 A2 * | 10/1997 | ................ 604/358 |
| JP | 7-303670 | 11/1995 | |
| WO | WO 96/23472 | 8/1996 | |
| WO | WO 9641602 * | 12/1996 | .......... A61F/13/15 |
| WO | WO 97/33545 | 9/1997 | |

* cited by examiner

Primary Examiner—Rodney M. Lindsey
Assistant Examiner—Angela J. Grayson
(74) Attorney, Agent, or Firm—Lowe Hauptman Gilman & Berner, LLP

(57) ABSTRACT

A sanitary napkin with a pair of wings includes a topsheet, a backsheet and an absorbent core disposed therebetween, the wings including a portion of the backsheet extending bilaterally of the napkin and a breathable sheet material bonded to the portion by means of bonding lines extending in a transversely direction of the napkin and arranged intermittently in a longitudinal direction of the napkin.

8 Claims, 2 Drawing Sheets

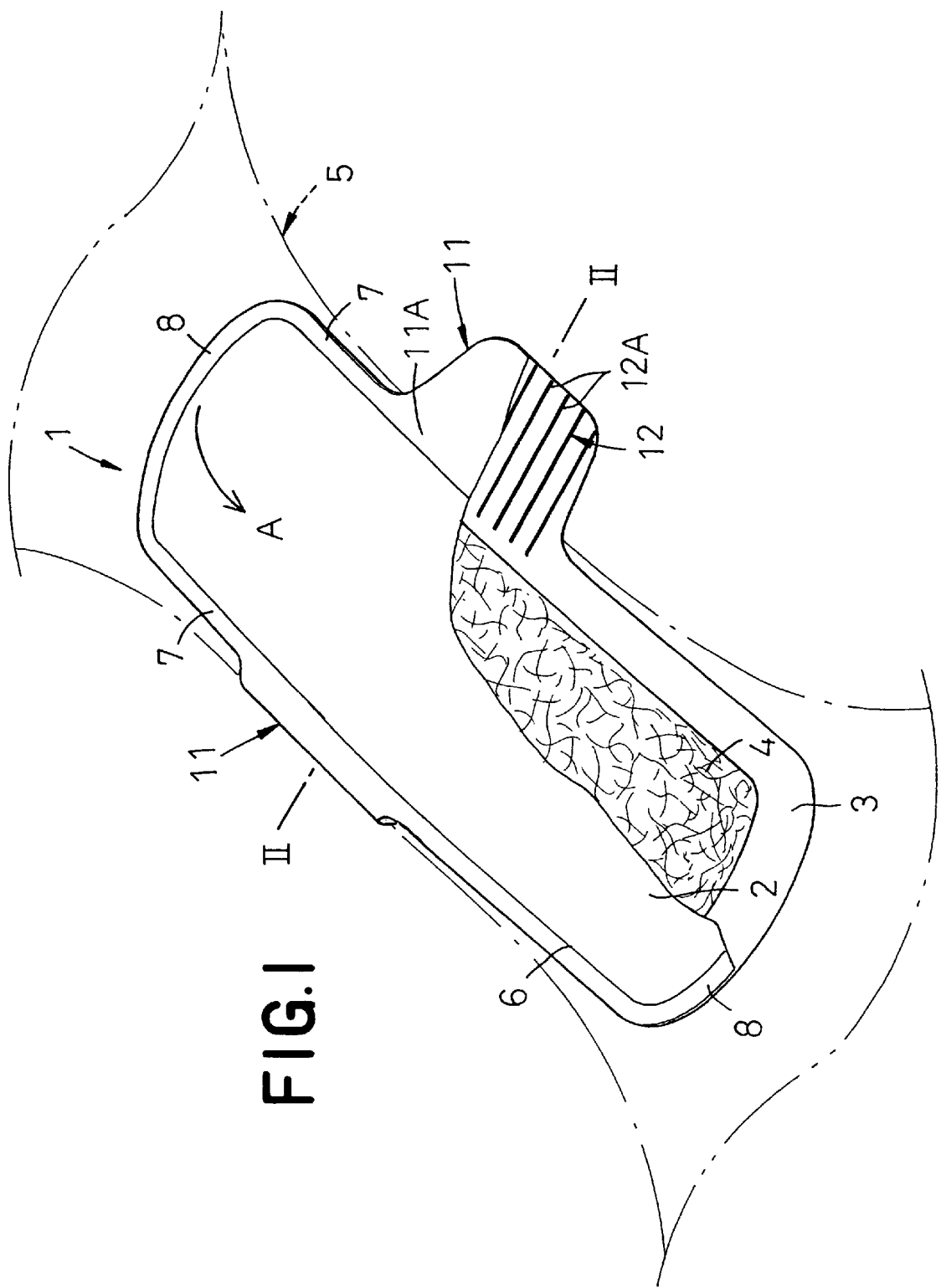

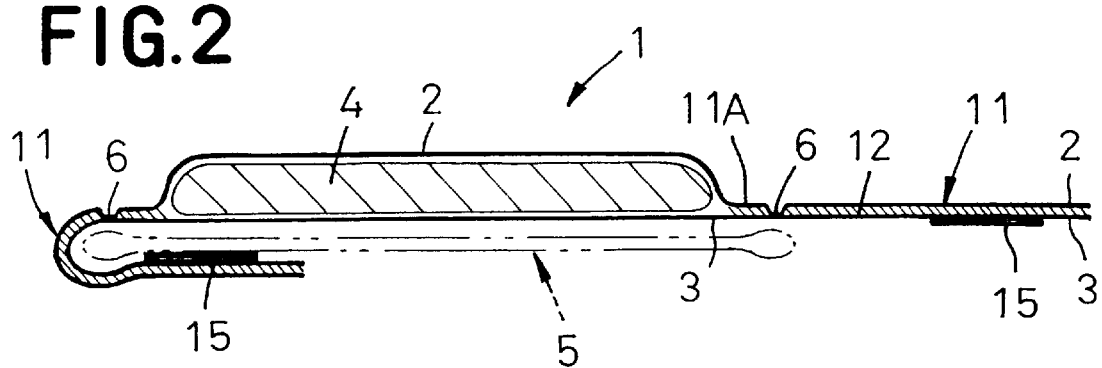
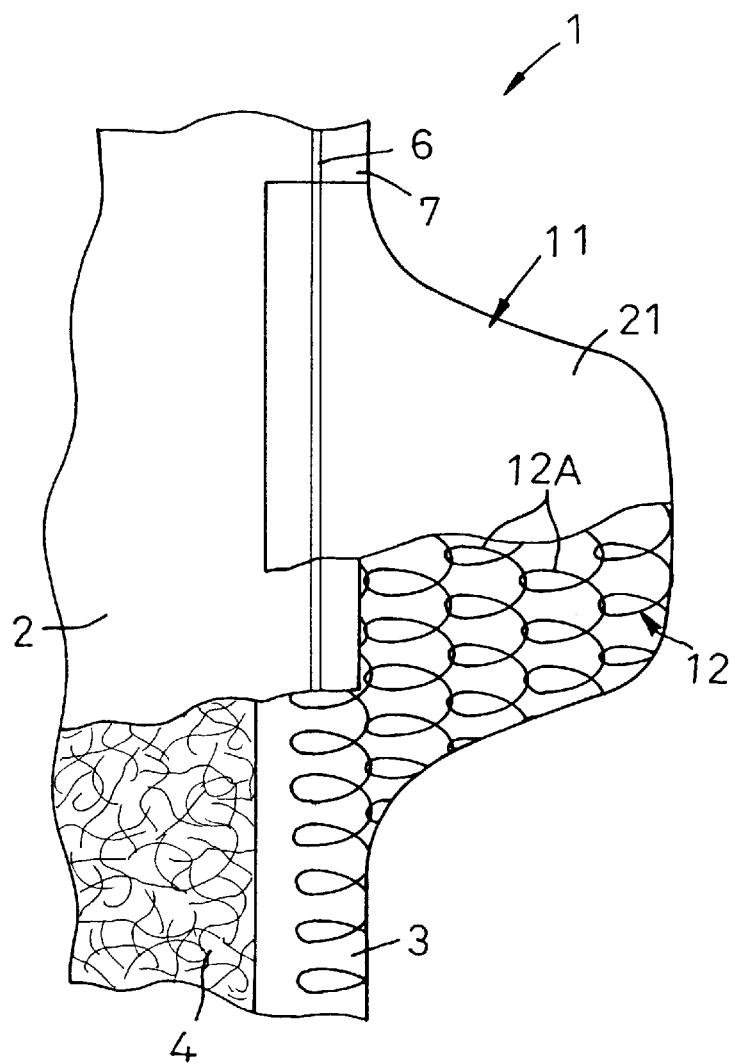

SANITARY NAPKINS PROVIDED WITH WINGS

BACKGROUND OF THE INVENTION

This invention relates to sanitary napkin provided with a pair of wings.

It is well known to provide a sanitary napkin with a pair of wings by bonding its topsheet and backsheet to each other, for example, from Japanese Patent Application Disclosure Gazette (Kokai) No. Hei7-303670. It is also well known that a breathable and liquid-impervious plastic film is sometimes used as material for a backsheet of a sanitary napkin. For example, extruded a film obtained from a mixture of polyethylene and fine particles of barium sulfate or calcium carbonate may be stretched to make such a plastic film.

The breathable/liquid-impervious plastic film made from foregoing mixture has a relatively low tear strength and therefore the wings formed by using the film as the backsheet has sometimes been torn at its proximal end longitudinally of the napkin as the wings are pulled to peel off the used napkin from the wearer's undergarment. While the topsheet may be bonded to the film as reinforcing means to improve the tear strength of the wings, the breathability of the film will be adversely affected in the regions of these wings depending on the manner of bonding. The wings are not necessarily folded, over their entire areas, onto the outer surface of the undergarment but sometimes partially left on the inner surface of the undergarment in contact with the wearer's skin. The wings sometimes partially left on the inner surface of the undergarment must be free from the concern that the particular manner of bonding might deteriorate the breathability of the film.

SUMMARY OF THE INVENTION

It is an object of this invention to provide a sanitary napkin having a pair of wings formed by a breathable/liquid-impervious backsheet so that a tear strength of the wings can be improved without deterioration of its breathability.

According to this invention, there is provided a sanitary napkin provided with a pair of wings, the sanitary napkin comprising a breathable/liquid-pervious topsheet, a breathable/liquid-impervious backsheet and an absorbent core disposed between the topsheet and the backsheet, the wings comprising a portion of the backsheet extending bilaterally of the napkin and a sheet material bonded to the bilaterally extending portion and said wings being formed on surfaces of the wings intended to be placed upon an undergarment with adhesively fastening zones, and the sheet material being of a breathable nature and bonded to the portion of the backsheet extending bilaterally of the napkin as well as to respective proximal ends of the portion by means of bonding lines extending in a transverse direction of the napkin and arranged intermittently in a longitudinal direction of the napkin.

According to one embodiment of this invention, the sheet material is a part of the topsheet.

According to another embodiment of this invention, the wings are coated with adhesive agent so as to describe a plurality of spirals and the bonding zones are substantially defined by portions of the spirally coated adhesive agent extending in the transverse direction of the napkin and arranged intermittently in the longitudinal direction of the napkin.

According to still another embodiment of this invention, an area percentage of the bonding zones occupying the wings is in a range of 3–60%.

According to further another embodiment of this invention, the napkin has a bonding line formed by heat-sealing to bond the topsheet and the backsheet along a periphery of the napkin and extends, in the vicinity of the respective proximal ends of the wings, in parallel to transversely opposite side edges of the absorbent core so that the sheet material is bonded to the backsheet also along the bonding line.

BRIEF DESCRIPTION OF THE DRAWINGS

FIG. 1 is a perspective view showing a partially cutaway sanitary napkin according to an embodiment of this invention;

FIG. 2 is a sectional view taken along a line II—II in FIG. 1; and

FIG. 3 is a fragmentary plan view showing an important part of a partially cutaway sanitary napkin according to another preferred embodiment of this invention.

DETAILED DESCRIPTION OF THE PREFERRED EMBODIMENTS

Details of a sanitary napkin provided with a pair of wings according to this invention will be more fully understood from the description given hereunder with reference to the accompanying drawings.

FIG. 1 is a perspective view showing a partially cutaway sanitary napkin 1 provided with a pair of wings and FIG. 2 is a sectional view taken along a line II—II in FIG. 1. Referring to FIGS. 1 and 2, a crotch region 5 of an undergarment to which the napkin 1 will be fastened is indicated by chain lines. The napkin 1 comprises a breathable/liquid-pervious topsheet 2, a breathable/liquid-impervious backsheet 3 and an absorbent core 4 disposed between these two sheets 2, 3. The topsheet 2 and the backsheet 3 extend outward beyond a peripheral edge of the absorbent core 4 and are placed one upon another in these extensions. The topsheet 2 and the backsheet 3 are bonded to each other along a bonding line 6 extending along their peripheral edges, leaving a marginal region extending outside the bonding line 6. The marginal region defines a pair of transversely opposite side edge flaps 7 which extend longitudinally of the napkin 1 and a pair of longitudinally opposite end flaps 8 which extend transversely of the napkin 1. The side edge flaps 7 partially extend outward to form a pair of wings 11. The bonding line 6 comprises suitable adhesive agent such as hot melt adhesive agent or a compression-sealed groove and extends in parallel to the side edges of the absorbent core 4 in the vicinity of proximal ends of the respective wings 11. FIGS. 1 and 2 illustrate one of the wings 11 folded onto the outer surface of the crotch region 5 and the other wing 11 extending laterally of the napkin 1. The wings 11 are releasably fastened to the crotch region 5 by means of adhesive agent 15 (See FIG. 2) applied to the lower surfaces of the respective wings 11.

Over the wings 11, the topsheet 2 and the backsheets 3 placed one upon another are bonded together in respective adhesive coated zones 12 each comprising a plurality of adhesive coated lines 12A extending transversely of the napkin 1 and arranged intermittently in the longitudinal direction of the napkin 1 on any one of these two sheets 2, 3 or in respective seal zones 12 each comprising the corresponding number of seal lines. An area of the adhesive coated zones 12, i.e., a total area of the adhesive coated lines 12A or an area of the seal zones 12 is preferably limited to 3–60% of an area of the wings 11 in order to alleviate a deterioration of the breathability of the sheets 2, 3. The adhesive coated lines 12A may sometimes extend to the respective side edge flaps 7 of the napkin 1 corresponding to proximal ends 11A of the respective wings 11.

Of the napkin 1 having such an arrangement, the breathable/liquid-pervious topsheet 2 may be formed by a nonwoven fabric of thermoplastic synthetic fibers or of rayon fibers having a basis weight of 10~80 g/m$^2$. Alternatively, the topsheet 2 may be also formed by other material such as a plastic film being 0.01~0.1 mm thick and formed with a plurality of apertures each having a diameter of 0.1–5 mm. The breathable/liquid-impervious backsheet 3 may be formed by a stretched film of polyethylene or the like containing 30~70% by weight of fine particles of barium sulfate or calcium carbonate. Such a film is very soft and offers a good touch and the wings 11 obtained using the film is also soft and offers a good touch. The intermittent arrangement of the adhesive coated lines or seal lines 12A forming the adhesive coated zones 12 or seal zones 12 on the respective wings 11 is important to maintain softness and good touch of the wings 11. The absorbent core 4 may be formed by fluff pulp or a mixture of fluff pulp and super-absorptive polymer particles. The adhesive coated zones 12 may be formed by coating the topsheet or the backsheet with, for example, hot melt rubber adhesive.

To wear the napkin 1, the respective wings 11 may be folded along peripheries of leg-openings of the crotch region 5 and fastened to the outer surface of the crotch region 5 by means of adhesive 15, as illustrated by FIGS. 1 and 2. After a single use, the napkin 1 is disposable in the conventional manner, i.e., the wings 11 may be peeled off from the crotch region 5 before its disposal. During this operation of stripping the napkin 1 from the crotch region 5, it may sometimes happen that the napkin 1 is lifted up in the direction as indicated by an arrow A before the wings 11 are completely peeled off from the crotch region 5. In this case, a tearing force is exerted longitudinally upon the proximal ends 11A of the respective wings 11. If the wings 11 are formed by using the breathable/liquid-impervious film alone, the proximal ends 11A will be torn off under the tearing force and consequently the wings 11 will be left on the crotch region 5 after the operation of stripping the napkin 1 from the shorts 5.

To avoid such a problem, the napkin 1 of this invention has its wings 11 reinforced by the topsheet 2 to have a sufficiently high tear strength to make the napkin wearer aware, before the wings 11 will be torn off, that the wings 11 are still not completely peeled off from the crotch region 5. The adhesive zones 12 of the respective wings 11 comprise a plurality of intermittently arranged adhesive lines 12A and there is no concern that the presence of these adhesive zones 12 may affect the desired breathability of the topsheet 2 and the backsheets 3. Consequently, the napkin 1 of this invention can avoid stuffiness and/or skin eruption even if the napkin I is put on the wearer's body with the wings 11 partially contacting the wearer's skin. As still another advantageous feature of this invention, the adhesive lines 12A extend transversely of the napkin 1 so that the wings 11 may be more effectively protected from being torn off longitudinally of the napkin 1 than the case in which the wings 11 extend longitudinally of the napkin 1.

FIG. 3 is a fragmentary plan view of a partially cutaway napkin 1 according to one preferred embodiment of this invention, showing the wings 11 and a region extending in the vicinity of the wings 11. Each of the wings 11 comprises the breathable/liquid-impervious backsheet 3 and an upper sheet 21 which is different from the topsheet 2 and formed by a nonwoven fabric made of thermoplastic synthetic fibers. These two sheets 3, 21 are bonded to each other by means of adhesive coated zone 12 defined by a plurality of adhesive spirals extending longitudinally of the napkin 1. The upper sheet 21 functions as a reinforcing sheet in the place of the topsheet 2 and extends inwardly of the napkin 1 until an inner side edge of the upper sheet 21 is placed upon the topsheet 2 along the side flap 7. The topsheet and the backsheet 3 and the upper sheet 21 are bonded together along the line 6. The adhesive coated zone 12 comprises a plurality of adhesive spirals 12A extending substantially in the transverse direction of the napkin 1 and spaced one from another in the longitudinal direction of the napkin 1. Each pair of the adjacent spirals 12A, 12A cooperate with each other to prevent the wing 11 from being torn off in the longitudinal direction with a similar effect achieved by the adhesive lines 12A rectilinearly extending in the transverse direction of the napkin 1 as shown in FIG. 1.

As will be apparent from the foregoing description, the sanitary napkin according to this invention has a pair of wings each comprising a laterally extending portion of the backsheet formed by the breathable/liquid-impervious plastic film and a reinforcing sheet bonded to the laterally extending portion. These two sheets are bonded to each other by means of an adhesive zone defined by a plurality of adhesive lines arranged intermittently in the longitudinal direction of the napkin so as to extend at least substantially in the transverse direction of the napkin. This unique arrangement of the adhesive zone enables the wings to maintain a desired breathability and, at the same time, prevents the wings from being easily torn off in the longitudinal direction of the napkin.

The topsheet and the backsheet are bonded to each other along a seal line defining a peripheral edge of the napkin so that the seal line extends in parallel to transversely opposite side edges of the absorbent core in the vicinity of proximal ends of the respective wings. According to such an arrangement, the seal line functions also to protect the portion of the backsheet laterally extending and/or the wings themselves against being torn off transversely of the seal line. In this manner, the previously described effect of preventing the wings from being easily torn off can be further improved.

What is claimed is:

1. A sanitary napkin having a pair of wings, said sanitary napkin further comprising a breathable and liquid-pervious topsheet, a breathable and liquid-impervious backsheet, and an absorbent core disposed between said topsheet and said backsheet;

each of said wings comprising a portion of said backsheet extending outwardly in a transverse direction of said napkin, a breathable sheet material bonded to said portion of said backsheet, and an adhesive fastening zone adapted to adhere to a garment of a wearer; and said sheet material being bonded to said portion of said backsheet by means of at least three bonding lines extending in the transverse direction of said napkin and arranged intermittently in a longitudinal direction of said napkin.

2. The sanitary napkin according to claim 1, wherein said sheet material is a part of said topsheet.

3. The sanitary napkin according to claim 1, wherein said wings are coated with an adhesive agent so as to describe a plurality of spirals, and said fastening zones are substantially defined by portions of said spirally coated adhesive agent extending in the transverse direction of said napkin and arranged intermittently in the longitudinal direction of said napkin.

4. The sanitary napkin according to claim 1, wherein an area percentage of said fastening zones occupying said wings is in a range of from about 3 to about 60%.

5. The sanitary napkin according to claim 1, wherein said napkin has a bondline formed by heat-sealing to bond said topsheet and said backsheet circumferentially of said absorbent core, said bond line extends, in the vicinity of the respective proximal ends of said wings, in parallel to transversely opposite side edges of said absorbent core, said sheet material is bonded to said backsheet also along said bondline.

6. The napkin of claim 1, wherein the bonding lines are distinct, unconnected and spaced from each other in the longitudinal direction of the napkin.

7. The napkin of claim 1, wherein the bonding lines are substantially parallel.

8. The napkin of claim 1, wherein the bonding lines extending for an entire width of said wing as measured in the transverse direction of the napkin.

\* \* \* \* \*

UNITED STATES PATENT AND TRADEMARK OFFICE
CERTIFICATE OF CORRECTION

PATENT NO. : 6,547,772 B1
DATED : June 5, 2003
INVENTOR(S) : Makoto Suekane

It is certified that error appears in the above-identified patent and that said Letters Patent is hereby corrected as shown below:

<u>Title page, Item [54] and Column 1, lines 1-2,</u>
Please amend the Title as follows:
-- SANITARY NAPKIN[S] PROVIDED WITH WINGS --.

Signed and Sealed this

Twenty-third Day of September, 2003

JAMES E. ROGAN
*Director of the United States Patent and Trademark Office*